United States Patent [19]
Abdel-Rahman

[11] Patent Number: 5,739,699
[45] Date of Patent: Apr. 14, 1998

[54] METHOD AND APPARATUS FOR ION DISCRIMINATION IN AN ELECTRON CAPTURE DETECTOR

[75] Inventor: Mahmoud F. Abdel-Rahman, West Grove, Pa.

[73] Assignee: Hewlett-Packard Company, Palo Alto, Calif.

[21] Appl. No.: 706,918

[22] Filed: Sep. 3, 1996

[51] Int. Cl.$^6$ .................................................. G01N 27/64
[52] U.S. Cl. .......................... 324/465; 324/468; 324/470; 250/382; 250/389
[58] Field of Search .................................... 324/459, 464, 324/465, 468, 469, 470; 250/374, 379, 382, 384, 385.1, 385.2, 389; 313/54

[56] References Cited

U.S. PATENT DOCUMENTS

| | | | |
|---|---|---|---|
| 3,566,107 | 2/1971 | Taylor et al. | 250/385.1 X |
| 4,063,156 | 12/1977 | Patterson | 324/465 |
| 4,264,817 | 4/1981 | Neukermans et al. | 250/379 |
| 4,304,997 | 12/1981 | Sullivan et al. | 250/379 |
| 4,651,008 | 3/1987 | Wells | 250/379 X |
| 4,684,807 | 8/1987 | Wells | 250/379 X |
| 4,733,086 | 3/1988 | Simmonds | 250/382 X |
| 4,740,695 | 4/1988 | Simpson | 250/282 |
| 5,479,022 | 12/1995 | Simon, Jr. | 250/382 |

OTHER PUBLICATIONS

Product Review—"Electron Capture Detection For GC", Analytical Chemistry, Jul. 1, 1995, pp. 439A–442A.
J.E. Lovelock—"The Electron Capture Detector–Theory And Practice", Journal of Chromatography, 99 (1974) 3–12 (month unavailable).
J.E. Lovelock—"Electron Capture Detector–Theory And Practice II", Journal of Chromatography, 158 (1978) 123–138 (month unavailable).
W.B. Knighton and E.P. Grimsrud—Linearization Of Electron Capture Detector Response To Strongly Responding Compounds, Analytical Chemistry, 1983, 55, 713–718 (month unavailable).
W.B. Knighton and E.P. Grimsrud—"Physical Parameters Affecting The Quantitative Response Of The Constant Current Electron–Capture Detector", Journal of Chromatography, 288 (1984) 237–252 (month unavailable).

G. Wells—"A Micro–Volume Electron Capture Detector For Use In High Resolution Capillary Column Gas Chromatography", Journal of High Resolution Chromatography & Chromatography Communications, vol. 6, Dec. 1983, pp. 651–654.

G. Wells and R. Simon—"Evaluation Of Electron Capture Cell Designs For Use In High Resolution Capillary Column Gas Chromatography", Journal of High Resolution Chromatography & Chromatography Communications, vol. 6, Aug. 1983, pp. 427–430.

Primary Examiner—Ernest F. Karlsen
Assistant Examiner—Diep Do
Attorney, Agent, or Firm—Mark Z. Dudley

[57] ABSTRACT

Electron capture detector for use with an effluent stream from a gas chromatograph includes an electron source means and an adjacent ionization chamber in which electron capture takes place. The active region of the ionization chamber is disposed to receive free electrons and a flow of purge gas. The detector has an inlet port for receiving a sample gas as well as an outlet port for exhausting the sample gas and the purge gas. A collector electrode in the detection chamber is biased so as to collect the free electrons in the absence of electrophilic substance. Electrophilic substances in the detector will reduce the flow of electrons to the collector and generate an ionic current. An insulative member in the form of a flow guide may be located at the portion of the anode so as to permit pulsing of free electrons to the anode but substantially block the ionic current, i.e., to discriminate between the free electrons and the ionic current. The addition of a fluid stream of purge fluid also provides a path for diverting the fluid mixture from the anode. The flow guide is configured to direct such fluid stream over the exposed portion of the anode, thus creating a fluid barrier to the anode contamination.

7 Claims, 6 Drawing Sheets

James J. Sullivan (Hewlett–Packard Co.)—"Approximation Of Electron Capture Response Factors For Highly Electrophilic Compounds", Journal of Chromatography, 87 (1973) 9–16 (month unavailable).

J.J. Sullivan and C.A. Burgett (Hewlett–Packard Co.)—"Non–Linearity In Constant Current Electron Capture Detection", Chromatographia, vol. 8, No. 4, Apr. 1975, pp. 176–179.

J.J. Sullivan and D.H. Smith—"A New Linear Electron Capture Detector With Extended Dynamic Range", Hewlett–Packard Co. Technical Paper No. 49, given at The Pittsburgh Conference, Cleveland, 1972 (month unavailable).

Sally S. Stafford and Bruce W. Hermann—"Design, Performance, And Use Of The Hewlett–Packard 5890 Series II Electron Capture Detector", Application Note 228–116, Hewlett–Packard Co., Jun. 1990.

METHOD AND APPARATUS FOR ION DISCRIMINATION IN AN ELECTRON CAPTURE DETECTOR

FIELD OF THE INVENTION

This invention relates generally to ionization detectors and more particularly to an electron capture type of detector for use in detecting the constituent gases of a sample eluted from a gas chromatograph.

BACKGROUND OF THE INVENTION

Electron capture detectors for gas chromatography are well known in the art. For example, a review of such detectors is contained in an article entitled "Electron Capture Detectors for GC", by Debra Noble, *Analytical Chemistry*, Jul. 1, 1995, pages 439A–442A. The electron capture detector is extremely sensitive to certain molecules such as alkyl halides, but is relatively insensitive to hydrocarbons, alcohols, ketones, etc. This type of detector features high sensitivity and high selectivity towards electrophilic compounds and is widely used for detecting trace amounts of pesticides in biological systems and in food products. Such compounds typically contain halogens which combine with free electrons in the detector. The resulting decrease in free electrons is monitored and used as an indication of the concentration of the test substances in a sample.

The electron capture detector can take several forms but all the forms are characterized by a flow-through chamber containing spaced apart, insulated electrodes and a source of ionizing radiation. FIG. 1 illustrates the general design of a prior art electron capture detector 100, such as the electron capture detector installed in the HP 5890 Series II gas chromatograph, produced by Hewlett-Packard Co., Palo Alto, CA. A generally cylindrical, electrically-pulsed metal electrode (anode) 115 is connected at its upper end to the upper body of the electron capture detector, separated therefrom by an insulator 116. The other end of the anode 115 projects into a lower region in a detection cell defined by an ionization chamber 120 having a grounded collector (cathode) 124. An outlet end of a separation column 111 is housed concentrically inside a fused silica liner 112 and an adapter 113. The placement of the column 111 in the liner 112 with respect to a make up gas feed line 114 is such that a passageway 118 is formed having an annular cross section between the inner wall of the liner 112 and the outer wall of the column 111. This passageway 118 in liner 112 is provided for passage of a make-up gas into the detector when, for example, the column 111 is a capillary column. The make-up gas is expected to be mixed with the effluent from the column 111. The top end of the chamber 120 is provided with side ports 121, 122. Side port 121 is typically connected to a pressurized supply of purge gas and side port 122 acts as a chamber vent.

The sample from the column 111 and the make-up gas from the passageway 118 are expected to enter the interior of the chamber 120 from below and travel upwards to the anode 115. Free electrons in the ionization chamber 120 are produced by radioactive beta emitters in the form of a foil or plating disposed inside the detector. Examples of such beta emitters are Tritium ($H^3$) and Nickel-63 ($Ni^{63}$). Thus, on the inner wall of the chamber 120 is a radioactive foil 125 which, in the illustrated example, is a $Ni^{63}$ radioactive source. The $Ni^{63}$ source ionizes the molecules of the make-up gas as it flows through the ionization chamber 120 and the electrons thus produced are caused to migrate to the anode 115, forming a pulsed electron current. This electron current becomes reduced if a sample containing electron-absorbing molecules is introduced; this loss of current can be amplified by an electrometer for analysis. Thus, when a sample component molecule comes into contact with the free electrons, the electrons may be captured by the sample molecule to create negatively charged ions. The voltage across the cell electrodes is pulsed to collect the remaining free electrons while the heavier ions are relatively unaffected and are swept with the carrier gas through the ionization chamber and out of the port 122.

In the preferred constant-current, variable frequency mode of operation, the cell current is measured and compared to the reference current. The pulse rate is then adjusted to maintain a constant cell current. When a sample compound that captures electrons is present, the pulse rate increases. The pulse rate is converted to a voltage and recorded. Hence, the pulse rate is the detector output signal.

The response of the typical electron capture detector has been observed to be dependant upon many variables, such as the molecular composition of the analyte and its concentration, the cleanliness and temperature of the detector cell, and the flow rates of the make-up gas and effluent. However, the behavior of the electron capture detector with regard many of these variables is not completely understood.

Chemical contamination and other factors operative in the ionization chamber may produce a d.c. voltage between the cathode and the anode known as the "contact potential". The contact potential causes a current of electrons and a migration of positive ions (ionic current) to flow to the anode, depending on the polarity of such d.c. voltage.

Another problem in a pulsed electron capture detector is that electrons may drift to the anode between the duration of pulses, causing a variation in the detector output signal baseline, due to the modulation of the effective reference current. The degree of this problem is again a function of the contact potential caused by contamination, and by the extent of the electron space charge. A conventional approach attempts to prevent this problem by biasing the anode to a small negative dc potential, that is, a d.c. potential greater than the worst case contact potential. However, such bias places a negative dc potential on the anode and causes a positive ionic current to be collected. The ionic current, which is usually variable and uncontrolled, causes the effective reference current and the baseline signal to vary to an extent which depends on the degree of contamination and the chemical structure of the contaminants. To minimize this effect of such variation, the conventional approach is to operate the electron capture detector at a high reference current. Unfortunately, high reference currents cause a high baseline frequency and a concomitant loss of dynamic range in the detector response.

Another source of drift (or even complete malfunction) in a typical electron capture detector is that the anode is subject to leakage current produced by surface contamination on the anode and the anode insulator. The subsequent increase in the reference current results in a higher baseline frequency, and again a loss of dynamic range in the detector response.

Accordingly, there exists a need for an electron capture detector having a detector response that exhibits an improved dynamic range.

SUMMARY OF THE INVENTION

The present invention is directed to methods and apparatus for achieving ion discrimination in an electron capture detector to thereby minimize the effect of contact potential on the detector response.

Detector response in an electron capture detector is based on an accurate measurement of the number of electrons captured by an electron capturing species. The reference current establishes the lowest electron capture detector pulse frequency and hence the frequency at which the lowest measurable concentration of the analyte is detected.

I have further determined that, as ions are much heavier than electrons, ion discrimination in an electron capture detector can be implemented by concealing the anode from drifting ions by suitable concealing means such that the ion drift no longer impinges on the anode. The effect of this ion discrimination (i.e., reducing this ion drift to the anode) offers a significant improvement in the electron capture detector performance. The contemplated electron capture detector may be operated at a reference current that is lower than the reference current level typically encountered in the prior art. As a result, the dynamic range of the detector response is found to be increased by approximately one order of magnitude. Also, the pulse frequency in a pulsed electron capture detector may be lowered, thus allowing more time for the generation of thermal electrons to reach equilibrium.

One feature of the present invention is thereby to provide an electron capture detector that employs a concealed anode so as to effect ion discrimination.

In another aspect of the invention, ion discrimination at the anode is particularly enhanced by provision of a flow guide which directs a purge gas fluid stream over the anode portion that may be subject to ion drift.

The accumulation of deposits and resulting contamination of the anode is prevented via this anode purge with a clean gas. A small proportion (e.g., 15–20%) of the purge gas is directed into the ionization chamber to purge the anode and the anode insulators. As a result, sample deposits on the anode and the insulators are reduced. A clean anode is then more efficient at electron collection, and clean insulators are subject to less electrical current leakage. As a result, the leakage current in the electron capture detector is reduced. Use of a small reference current allows the electron capture detector to operate at a lower baseline frequency. Consequently, the electron capture detector is capable of useful operation over a greater dynamic range.

Accordingly, the present invention relates generally to a improved electron capture detector for use with high resolution capillary columns in gas chromatography and in particular to a method and apparatus of increasing ion discrimination of the ionic current with respect to the anode, thereby reducing the effect of ionic current in the reference current.

It is a feature to provide an electron capture detector which is characterized by improved measurement of electron charge density versus analyte concentration by reducing the effect of contact potential and ionic current.

It is another feature to minimize or eliminate loss of linearity of response of the electron capture detector due to extraneous influences such as are caused by contamination encountered at the anode.

It is still another feature to minimize or eliminate baseline drift caused by contact potentials formed by chamber contaminants, by concealing the anode from the reaction chamber, thus preventing the travel of positive ions to the anode.

In a particular embodiment of the present invention, the desired concealing of the anode is provided by a flow guide that receives purge gas flow so as to create a fluid barrier to incident ion drift.

It is still another feature to minimize or eliminate baseline drift due to leakage current across the flow guide by proper choice of the a highly insulative material.

According to the preferred embodiments of the invention, there are provided an electron source means and an adjacent ionization chamber in which electron capture takes place. The active region of the ionization chamber is disposed to receive free electrons and also receive a flow of purge gas. The detection chamber has an inlet port for receiving a sample gas as well as an outlet port for exhausting the sample gas and the purge gas. A collector electrode in the detection chamber is pulsed so as to collect the free electrons in the absence of electrophilic substance. Under appropriate conditions, the presence of electrophilic substances in the detection chamber will reduce the flow of electrons to the collector. The resulting change in current flow to the collector electrode is a measure of the quantity of the electron capturing constituent in the sample gas.

The operating principles of the ion discrimination in the preferred embodiment may be understood as follows. Concealment of the anode is achieved by locating an insulative member in the form of a flow guide at the portion of the anode that is exposed to the aforementioned ionic current. The flow guide is located and configured so as to permit electron diffusion to the anode but block at least a substantial amount of the ionic current from the anode, i.e., to discriminate between the free electrons and the ionic current.

The addition of a stream of purge fluid also provides a path for diversion of the fluid mixture from the anode. The flow guide is preferably configured to direct such purge fluid stream over the exposed portion of the anode. This greatly reduces the contamination of the anode. As a result, the ions and the slowly-moving, negatively-charged sample molecules largely remain within the active region of the ionization chamber, or are swept away from the anode by the purge gas fluid.

DETAILED DESCRIPTION OF THE PREFERRED EMBODIMENTS

The apparatus and methods of the present invention may be employed in particular to improve the detection of an analyte that may be present in a variety of fluids. Gases are 'the preferred fluids according to the practice of the present invention, and therefore the following description of the invention will include a description of the arrangement, construction, and operation of a novel electron capture detector for use in a gas chromatographic analytical system (hereinafter, a chromatograph).

Figures 1A, 1B:
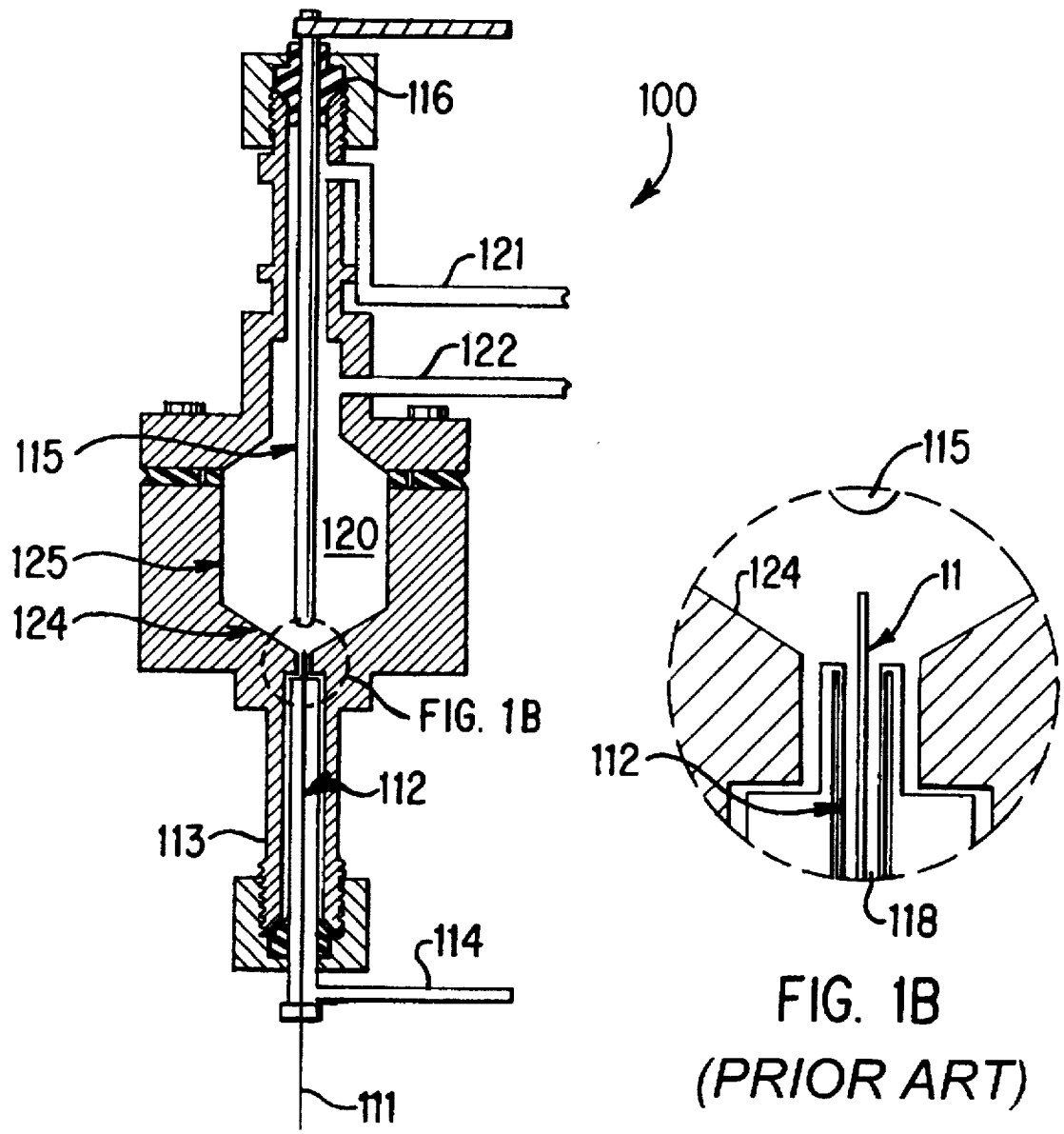
FIG. 1 is a schematic cross-sectional view of a prior art electron capture detector.
Figure 2:
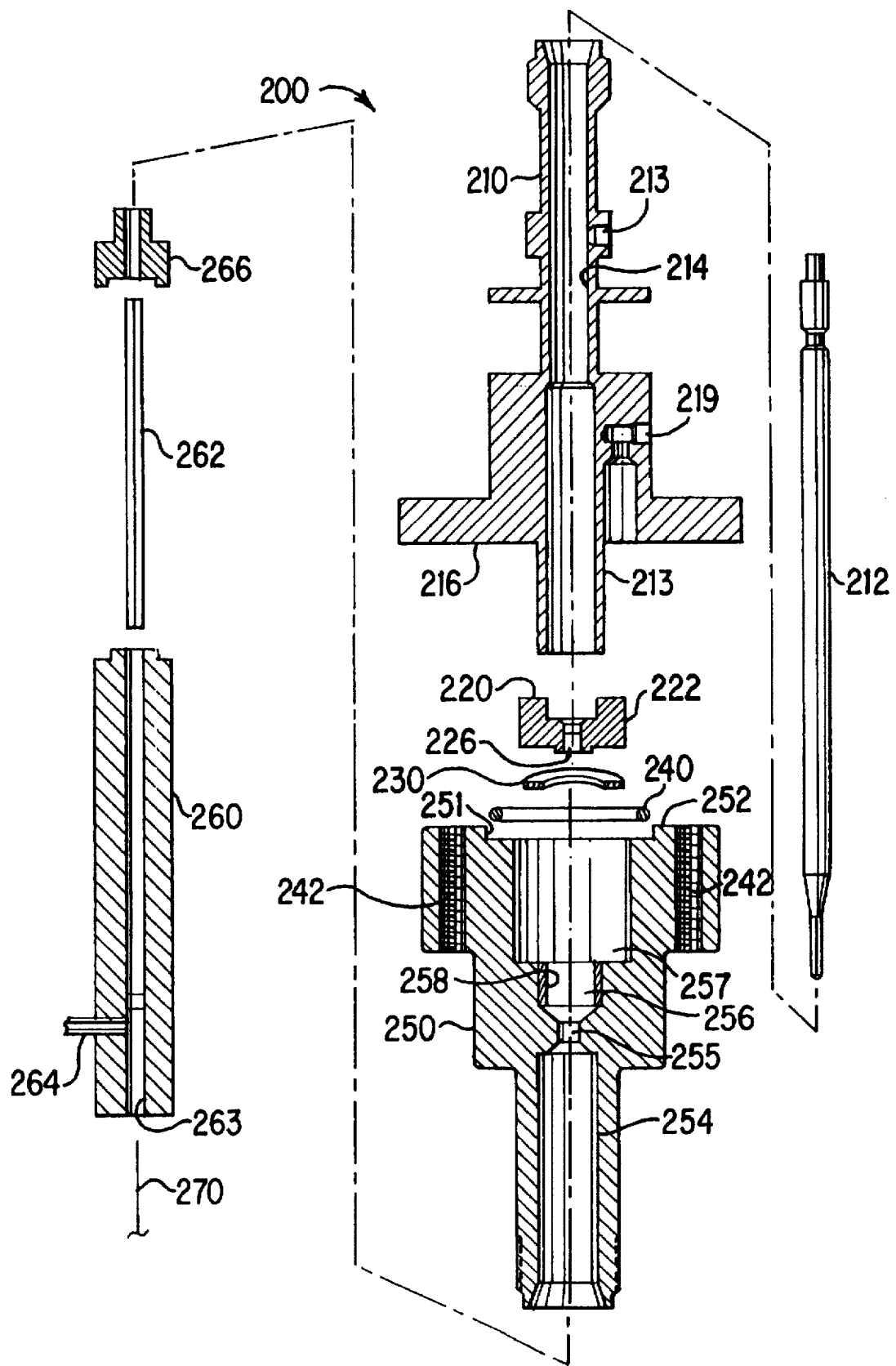
FIG. 2 is an exploded cross-sectional view of an electron capture detector of the present invention.
Figure 3A:
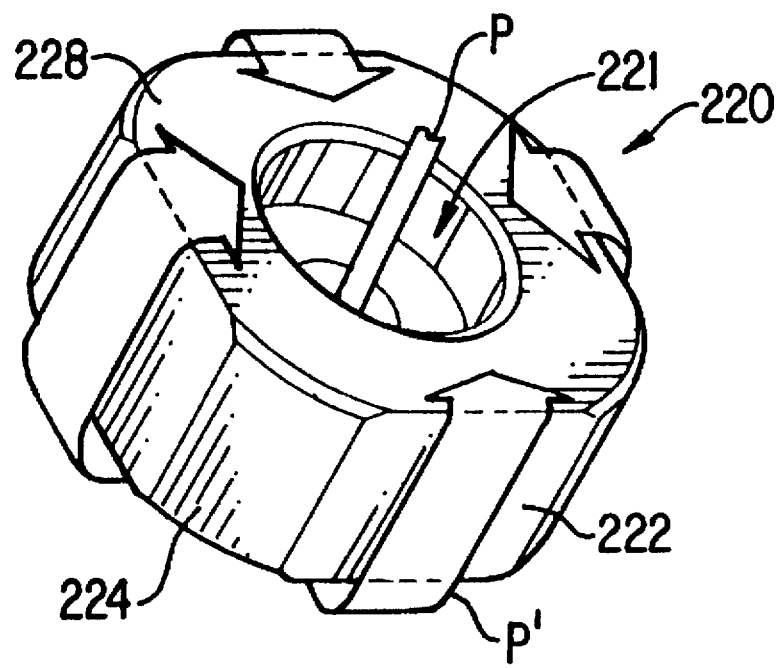
FIGS. 3A, 3B are perspective cross-sectional views of a preferred design for a flow guide for concealing the anode in the detector shown in FIG. 2.
Figure 3B:
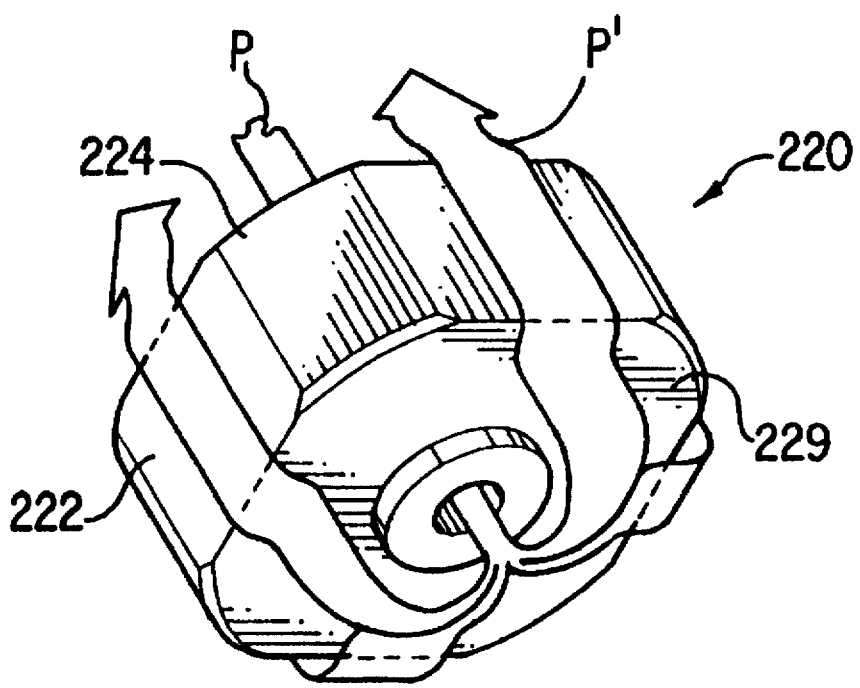
Figure 4:
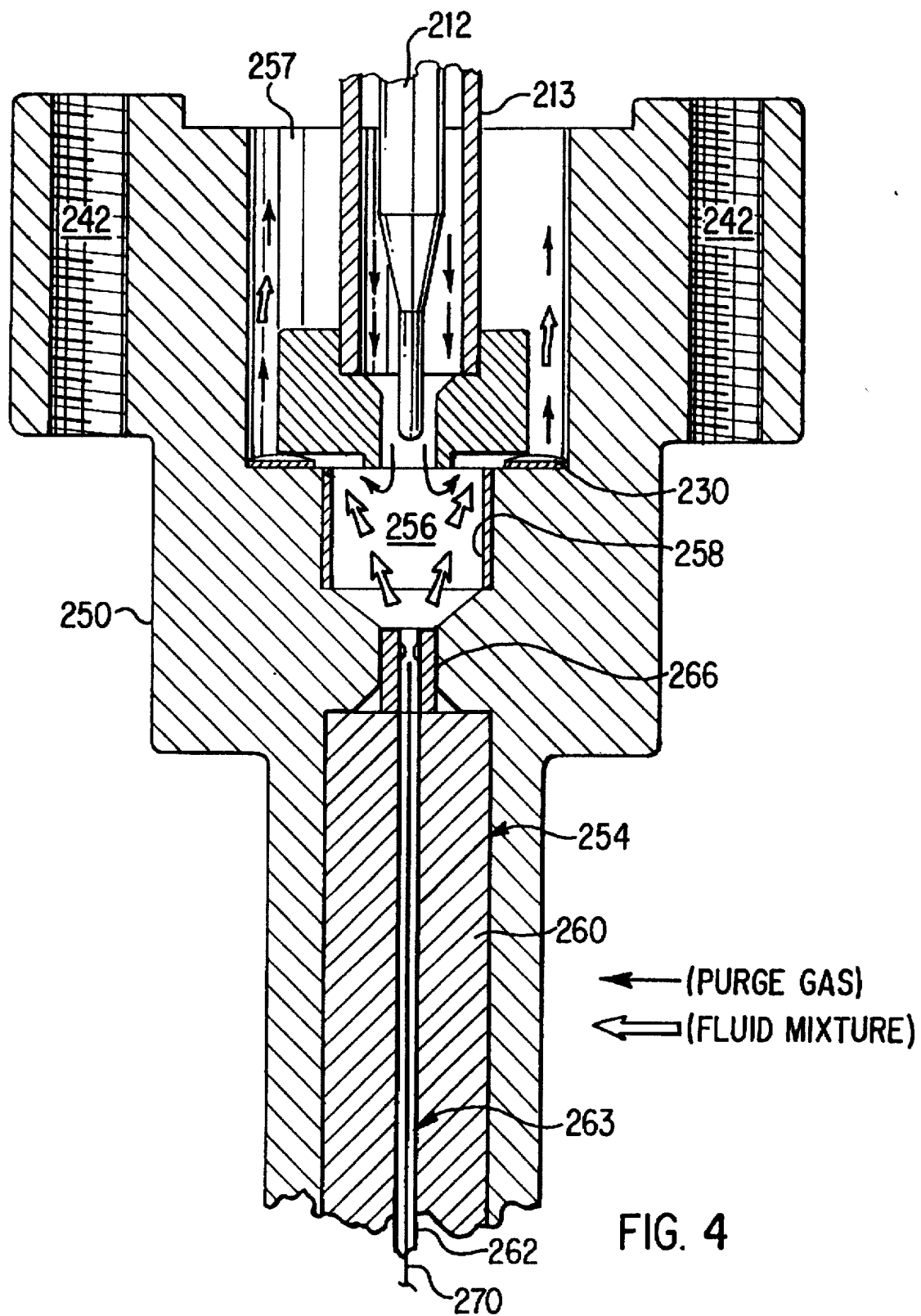
FIG. 4 shows an inlet system operable in the electron capture detector of FIG. 2.

Embodiments of the invention described herein are contemplated for use as a temperature-controlled, constant-current, pulse-modulated electron capture detector in a gas chromatograph. The preferred operation of the contemplated detector with respect to a conventional gas chromatograph may be understood as follows. In a chromatographic separation of a given sample compound, a sample is injected with a pressurized carrier gas into a separation column and the column effluent is directed as a fluid stream into the electron capture detector. One or more pneumatic manifold assemblies are envisioned, each of which serves in part to control and redirect a plurality of gas flows, including the carrier gas and a plurality of detector gases of appropriate types such as air, hydrogen, and make-up gas. Accordingly, the pneumatic manifold may be operated to effect a modulation of any of the aforementioned gas flows, and in particular to supply modulated purge gas flow and make-up gas flow to the electron capture detector described hereinbelow. Aspects of such fluid supply in the embodiments illustrated in FIGS. 2 et seq. is preferably provided via electronic pneumatic control (EPC). For further details of electronic pneumatic control techniques, one may consult, for example, Klein, et al., U.S. Pat. No. 4,994,096 and U.S. Pat. No. 5,108,466, the disclosures of which are incorporated herein by reference.

As illustrated in FIGS. 2–5, a preferred embodiment 200 of an electron capture detector constructed according to the invention includes an upper body 210, anode 212, flow guide 220, curved washer 230, seal 240, lower body 250, and adapter 260. The upper body 210 is operable as a collector electrode and includes an anode tube 213 that defines a central bore 214 for accommodating the anode 212 in a spaced, concentrically located position therein. The flow guide 220 and an electrically insulating insert (not shown, but typically mounted in the upper end of the central bore 214) are preferably formed of high purity alumina to ensure that the anode 212 is properly positioned and electrically isolated from the upper body 210.

The lower body 250 includes a recess 251 in an interface 252 for receiving the seal 240 and for receiving a corresponding mating surface 216 on the upper body 210. The lower body 250 includes a plurality of coaxially displaced, interconnected interior chambers which are in fluid communication therebetween: a central bore 254, a cap relief 255, an ionization chamber 256 having therein a radioactive source 258, and anode chamber 257. The curved washer 230 and flow guide 220 are locatable in the anode chamber 257 such that the uppermost surface of the flow guide 220 is closely fits onto the opposing surface of the anode tube 213. The upper body 210 also includes a purge flow inlet 218 which communicates with the central bore 214 and a purge flow outlet 219 which communicates with the anode chamber 257. Hermetic sealing between the mating surfaces 216, 252 is provided by compression of the seal 240 by appropriate clamping means such as screws extending through screw bores 242 into suitable receiving means (not shown) that may be located on or in the upper body 210. The upper body 210, lower body 250, and certain components therein (such as the curved washer 230) are preferably constructed of inert, heat resistant material such as stainless steel. The adapter 260, upper body 210, and lower body 250 may be heated to a selected temperature by means (not shown) as known in the art.

An outlet end of a chromatographic column 270 is positioned in a liner 262 and the column/liner assembly is located in the central bore 263. Gas to be analyzed, such as the effluent (E) from the chromatographic column 270 is conducted within the column 270. Make-up fluid (M) is thereafter supplied into the central bore 263 and into a central bore of the liner 262 by a make-up gas feed 264. A fluid mixture (F) composed of a substantially uniform mixture of the make-up gas (M) and the column effluent (E) are then passed into the central bore 254 from an adapter cap 266. Thus, when the adapter 260 is fully inserted into the central bore 254, the fluid mixture (F) exits the cap 266 and immediately enters into the ionization chamber 256.

The flow guide 220 is located at the uppermost portion of the ionization chamber 256 to effect an uppermost boundary to the active volume of the ionization chamber 256, the latter being defined as the region from which electrons are collected for measurement. Hence the active region is situated below the flow guide 220, thereby separating the anode 212 from the active volume. For this purpose, the flow guide 220 is made of a highly insulative material, such as a high purity alumina composition marketed as AL-300 and available from Wesgo/Duramic Precision Engineering Ceramics, Fairfield, N.J. The flow guide 220 is generally shaped like a disk, having a generally cylindrical section, upper and lower major surfaces 228, 229, side walls of alternating flat sections 222 and curved sections 224, and a recessed section 221 at its upper major side having an interior diameter sized for engaging and closely fitting a portion of the bottom exterior of the anode tube 213. The flow guide 220 is thus sized such that the curved sides 224 are sealing engaged with the interior of the anode chamber 257 when the flow guide 220 slides into the anode chamber 257. However, the presence of the curved washer 230 and the flat sides 222 allow the passage of purge gas (P) that originates from the purge flow inlet 218 and travels through the central bores 214 and 226 so as to be redirected (illustrated as purge gas P') over the lower major surface 229 of the flow guide 220. The lower major side 229 of the flow guide 220 faces into the ionization chamber 256 and thus towards the outlet end of the column/liner assembly.

The ionization chamber 256 has a cup-shaped section with the radioactive source 258 on its side wall being so designed and positioned such that the fluid mixture (F) can pass upwardly into the ionization chamber 256 for subsequent ionization of the sample molecules that are present in the fluid mixture (F). Further flow of the fluid mixture (F) is partially constrained by the lower major surface 229 of the flow guide 220 and by a fluid barrier provided by the purge gas flow (P') from a central bore 226 in the flow guide 220. That is, the fluid mixture (F) is prevented from contacting the anode 212 and is made to exit the ionization chamber 256 along the flat portions 220 of the side wall of the flow guide 222. Thus, the anode 212 is not actively swept by the fluid mixture (F). As a result, the anode 212 is effectively separated by the flow guide 220 from the fluid mixture (F) and the potential for contamination of the anode 212 by compounds in the fluid mixture is greatly reduced.

Figure 5:
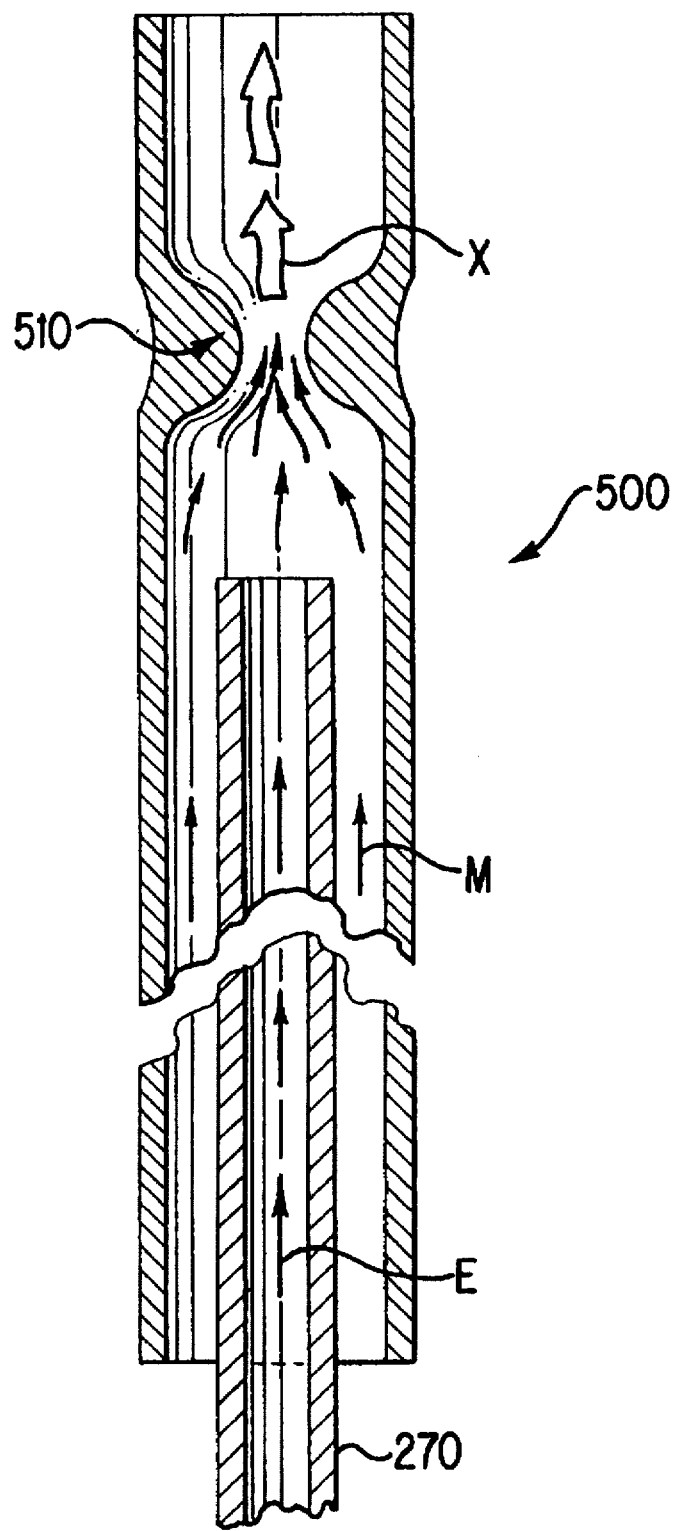
FIG. 5 is a cross-sectional view of an embodiment of a column liner constructed according to the invention to include a flow acceleration region for effecting a uniform mixture of column effluent and make-up gas.

As illustrated in FIG. 5, the desired mixing of the effluent and make-up gas is preferably implemented by a mixing device provided in the form of a hollow, tubular liner 500 formed of deactivated quartz and having a flow acceleration region 510 wherein the make-up gas and the effluent are subject to a momentary but substantial increase in velocity, thus causing turbulent flow within the flow acceleration region 510. The desired turbulent flow provides a substantially uniformly mixed product of the effluent (E) and the make-up gas (M). The flow acceleration region 510 is preferably provided by localized reduction of the internal diameter (I.D.) of the liner to a value that is approximately one-half to one-quarter of the average internal diameter. In one prototype of the liner 500, successful mixing was effected by a reduction of an average internal diameter of approximately 1000 micrometers to approximately 300 micrometers.

Another preferred aspect of the illustrated embodiment is that the portion of the liner 500 that is located downstream from the flow acceleration region 510 include a sufficiently large internal diameter such that the rate of flow of the fluid mixture (F) is slowed in comparison to the flow rate of the effluent (E). The relatively slow rate of entry of the fluid mixture (F) encourages a more uniform distribution of the sample molecules in the ionization chamber as the fluid mixture (F) flows into the ionization chamber 256.

Figure 6:
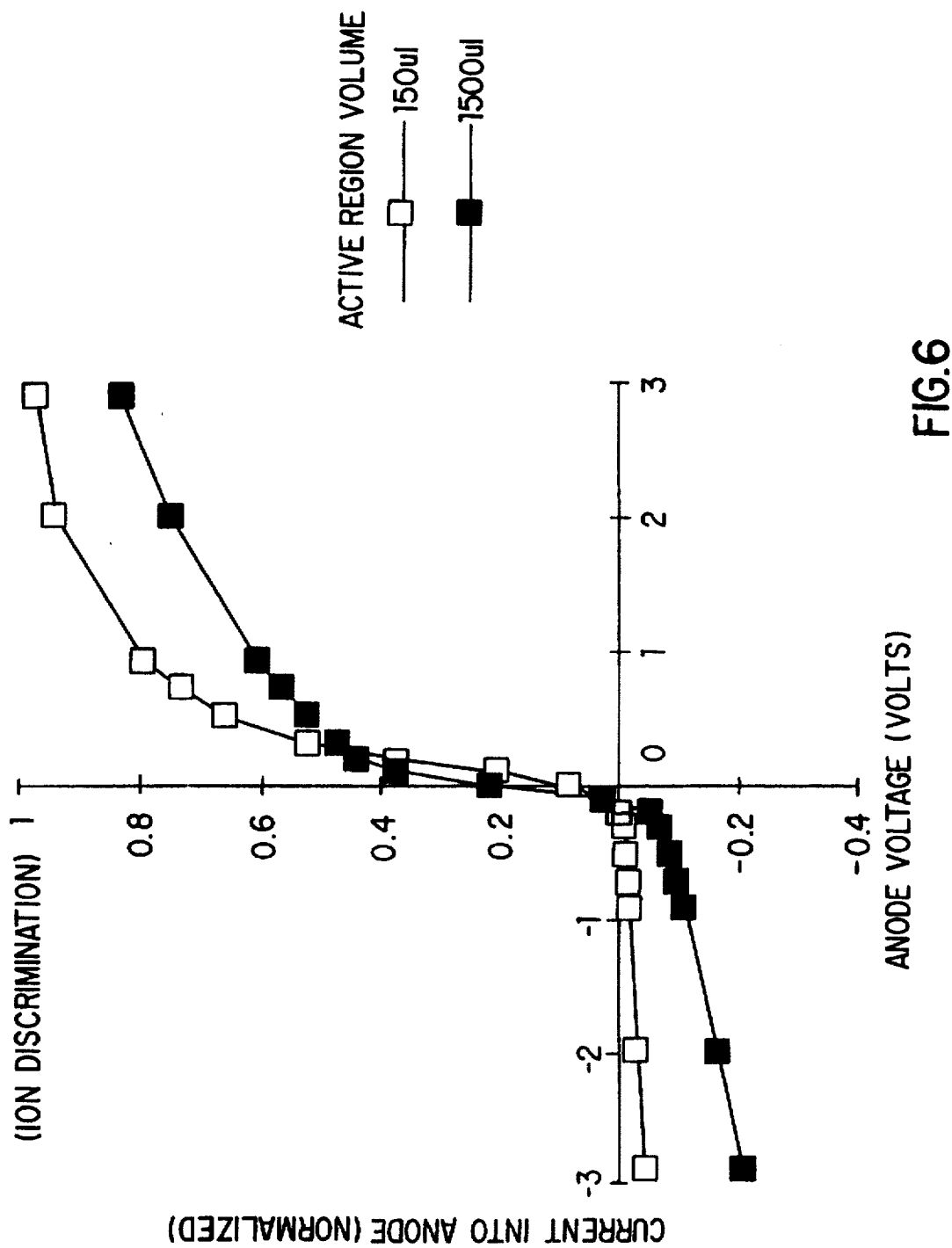
FIG. 6 is a graph showing experimental verification of the benefits of the present invention in a prototype of the electron capture detector of FIG. 2.

As illustrated in FIG. 6, data representative of the increase in ion discrimination by a prototype version of the illustrated electron capture detector 200 are shown. A first curve was obtained from a conventional electron capture detector having an active region volume of 1500 microliters in the ionization chamber, and a second curve was obtained from the prototype version of an electron capture detector having an active region volume of 150 microliters and constructed according to the present invention. With reference to the negative anode voltage region, one may see the result of ion discrimination in the reduction of the ionic current, when comparing the curves resulting from the prior art electron capture detector and the prototype version of the electron capture detector 200.

What is claimed is:

1. An electron capture detector for use with a gas chromatography column and a source of make-up gas, comprising:

an ionization chamber having an entrance opening and an exit opening;

sample inlet system operably connected between said column and the entrance opening for receiving column effluent and a fluid stream of said make-up gas and for directing a fluid mixture of column effluent and make-up gas through said entrance opening into said ionization chamber;

an electron source associated with said ionization chamber for generating a plurality of thermal electrons in said fluid mixture, whereby the presence of electron-capturing species in the fluid mixture may react with the thermal electrons;

anode electrode means and collector electrode means located with respect to said fluid mixture for detecting a subsequent variation in the thermal electron concentration in the fluid mixture; and an insulative member interposed between said fluid mixture in the ionization chamber and the anode electrode means having means for concealing the anode electrode means from an ionic current to thereby effect ion discrimination.

2. The electron capture detector of claim 1, further comprising:

an anode chamber located adjacent the exit opening of the ionization chamber and having means for locating the anode within the anode chamber and proximate the exit opening, the anode thereby having a portion thereof located proximate to the fluid mixture in the ionization chamber;

and wherein the insulative member further comprises a flow guide disposed between said anode portion and said ionization chamber, whereby said anode is substantially shielded from said ionized fluid.

3. The electron capture detector of claim 2, wherein the anode chamber includes an inlet port for receiving a purge gas flow and wherein said flow guide is located adjacent said portion and includes means for receiving said purge gas flow and interposing the received purge gas flow between said anode portion and the fluid mixture, said flow guide further including means for subsequently exhausting said purge gas from the vicinity of the anode portion, whereby said ion discrimination is enhanced.

4. The electron capture detector of claim 3, wherein the anode chamber and the ionization chamber are generally cylindrical and coaxially arranged, the anode being configured as an elongated member concentric with the anode chamber and having a tip located proximate the ionization chamber, and said flow guide being configured as a disc having upper and lower major sides, said lower side being configured to close an upper boundary of said ionization chamber and the upper major side being configured to close a lower boundary of the anode chamber, the disc having a central bore communicating between the upper and lower major surfaces for receiving the tip therein and for directing the purge gas through the central bore and over the tip, and the disc having means for subsequently directing the purge gas away from the tip and over a peripheral portion of the disc for exhausting the purge gas flow.

5. The electron capture detector of claim 1, wherein the flow guide is composed of alumina.

6. The electron capture detector of claim 1, wherein said electron source is a radioactive isotope.

7. Method for electron capture detection for use with a gas chromatography column and a source of make-up gas, comprising the steps of:

providing an ionization chamber having an entrance opening and an exit opening;

providing a fluid mixture of column effluent and make-up gas to flow through said entrance opening into said ionization chamber; and operating an electron source associated with said ionization chamber for generating a concentration of thermal electrons in said fluid mixture, whereby the presence of electron-capturing species in the fluid mixture may react with the thermal electrons;

locating anode electrode means and collector electrode means with respect to said fluid mixture for detecting a subsequent variation in the thermal electron concentration in the fluid mixture; and interposing an insulative member between said fluid mixture in the ionization chamber and the anode electrode means for concealing the anode electrode means from an ionic current to thereby effect ion discrimination.

* * * * *